Jan. 4, 1966 D. L. ARMSTRONG Plant Pat. 2,585
ROSE PLANT
Filed Oct. 13, 1964
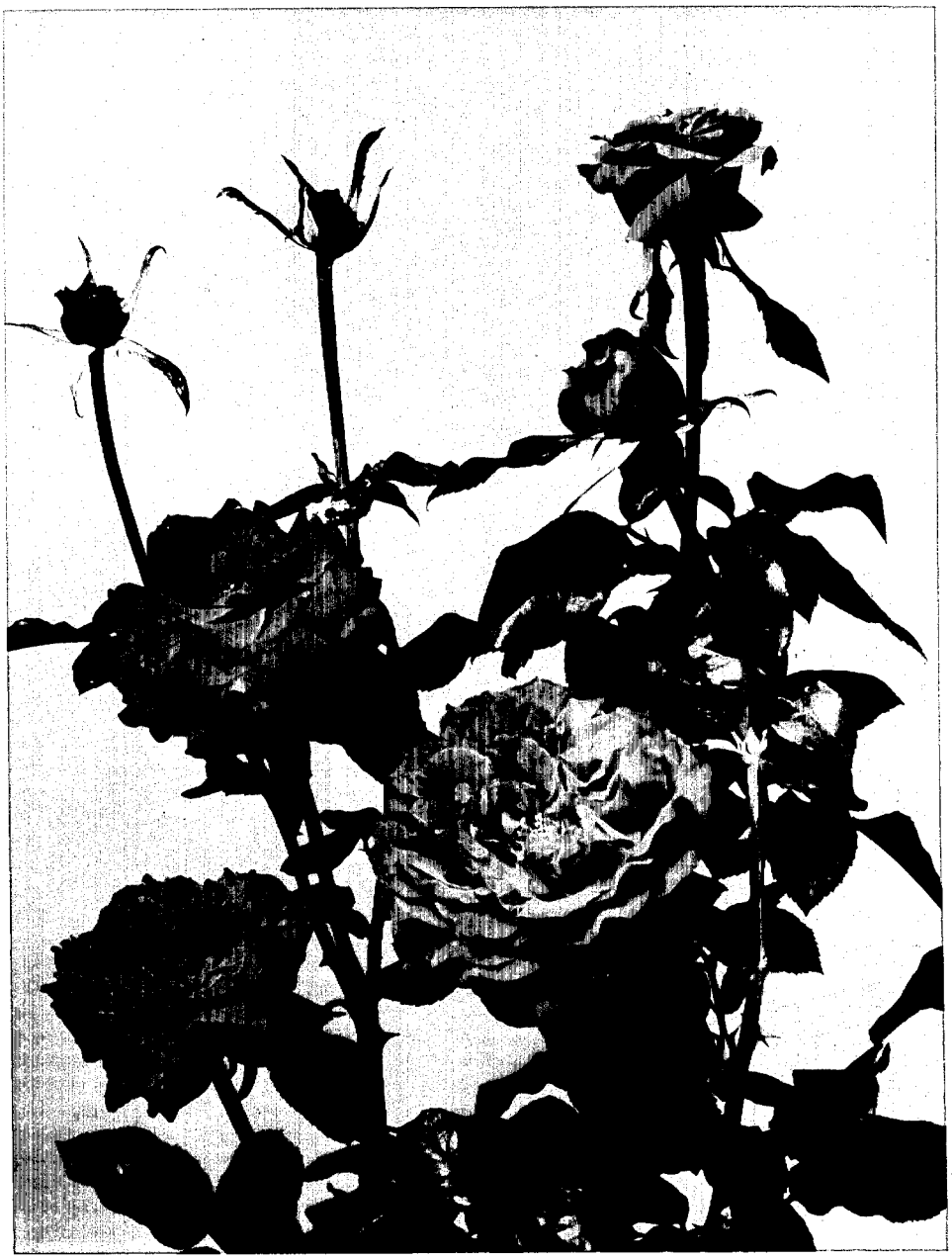
Inventor.
D. L. Armstrong
By: Robb & Robb
Attorneys.

United States Patent Office

Plant Pat. 2,585
Patented Jan. 4, 1966

2,585
ROSE PLANT

David L. Armstrong, Ontario, Calif., assignor to Armstrong Nurseries, Inc., Ontario, Calif., a corporation of California Filed Oct. 13, 1964, Ser. No. 403,671
1 Claim. (Cl. Plt.—21)

The present invention relates to a new and distinct variety of rose plant of the hybrid tea class, which was originated by me by crossing the variety "Queen Elizabeth" (Plant Patent No. 1,259) with the variety "Bravo" (Plant Patent No. 983).

The primary objective of this breeding was to produce a new and improved rose variety of the Grandiflora or hybrid tea type, having a plant habit comparable to that of the parent variety "Queen Elizabeth," combined with fairly double and Bright Red flowers of good form, comparable to the flowers of the parent variety "Bravo." This objective was fully achieved, along with other desirable improvements, as evidenced by the following characteristics which are outstanding therein and which distinguish it from its parents, as well as from all other varieties of which I am aware:

(1) A vigorous, upright-spreading and well branched plant habit;
(2) Attractive, large, leathery and semi-glossy foliage;
(3) A habit of bearing the flowers usually singly and abundantly on relatively long and strong stems;
(4) The production of large, extremely double flowers having an attractive, gracefully irregular or wavy form reminiscent of old-fashioned roses;
(5) A distinctive and attractive Bright Red flower color;
(6) Very long-lasting flower qualities, both as cut flowers and on the plant with the ability of holding the form and Bright Red color very well; and
(7) An ability of the flowers to clean well from the plant.

In comparison with its seed parent, "Queen Elizabeth," the flowers of the new variety have considerably more petals, and the flower color is Bright Red, as distinguished from the Pink flowers of this parent.

As compared with the pollen parent, "Bravo," the new variety has a much more vigorous plant habit, and the flowers have considerably more petals than those of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated.

Type: Tall; bush; outdoor; seedling; for cut flowers and for garden decoration.
Class: Hybrid tea.
Breeding: Seedling.
*Seed parent.*—"Queen Elizabeth."
*Pollen parent.*—"Bravo."
Propagation: Holds its distinguishing characteristics through succeeding propagations by budding.

*Flower*

Locality where grown and observed: Ontario, California.
Flowers borne: Usually singly, but sometimes 2 or 3 or more to stem; in irregular clusters; on strong, long stems.
Quantity of bloom: Free, outdoors.
Continuity: Nearly continuous during growing season.
Fragrance: Slight.
Bud:
*Peduncle.*—From average length to long; heavy; erect; usually smooth; with from none to few small stipitate glands and from none to few hairs.
*Color.*—Near Courge Green, Plate XVII (R), overlaid with near Buffy Brown, Plate XL (R) on side exposed to sun.
*Before calyx breaks.*—Size—medium. Form—Short; between ovoid and globular.
*As calyx breaks.*—Color—between Dahlia Purple, Plate 931/1, page 178 (W) and Plum Purple, Plate 934, page 179 (W).
*Sepals.*—Inner surface—with fine, wooly tomentum; sepals usually having foliaceous appendages extending ½ or more of sepal length. Outer surface—usually with several to many small stipitate glands. Alternate margins—lined with fine wooly tomentum. Other margins—with from several to many small stipitate glands and small to medium size foliaceous parts.
*As first petal opens.*—Size—between small and average. Form—from short to medium length; between ovoid and globular. Color—outside: Between Cardinal Red, Plate 822/1, page 168 (W) and Chrysanthemum Crimson, Plate 824, page 169 (W), blending with near Ruby Red, Plate 827, page 171 (W) toward base of petal. Inside—near Currant Red, Plate 821/1, page 167 (W), blending with near Indian Lake, Plate 826/1, page 170 (W) toward base of petal.
*Opening.*—Open up well; is not retarded or prevented from opening by cold, hot, wet or dry weather.
Bloom:
*Size (when fully open).*—Large; from 4 inches to 5 inches.
*Petalage.*—Very double; from 80 to 100 petals, plus 8 to 16 petaloids; arranger irregularly.
*Form.*—Cupped and high-centered at first, and remaining high-centered through maturity; outside and intermediate petals of both newly opened and three-days open flower usually reflexed outward along edges of petal; apex of outside petals sometimes also reflexed outward; inside and intermediate petals usually wavy, making them rigid and supporting each other, giving flower a ruffled appearance.
Petals:
*Texture.*—Medium thickness; moderately leathery.
*Appearance.*—Inside—slightly velvety. Outside—satiny.
*Shape.*—Outside—between round and broadly obovate, with apex flat. Intermediate—broadly obovate, with apex from rounded to flat. Inside—narrowly obovate, with apex rounded.

This description of a newly opened flower was made from a rose grown outdoors during the month of September at Ontario, California:

*Color.*—Outer petal—outside surface: between Rose Red, Plate 724, page 158 (W) and Chrysanthemum Crimson, Plate 824/3, page 169 (W); inside surface: between Cardinal Red, Plate 822/3, page 168 (W) and Chrysanthemum Crimson, Plate 824/3, page 169 (W). Intermediate petal—outside surface: near Currant Red, Plate 821/3, page 167 (W), blending with near Chrysanthemum Crimson, Plate 824/3, page 169 (W); inside surface: near Currant Red, Plate 821/3, page 167 (W), blending with near Currant Red, Plate 821, page 167 (W) toward base of petal. Inner petal —outside surface: near Indian Lake, Plate 826, page 170 (W); inside surface: near Indian Lake, Plate 826, page 170 (W).

This description was made from a rose that was open for three days outdoors during the month of September at Ontario, California:

*Color.*—Outer petal—outside surface: between Cardinal Red, Plate 822/2, page 168 (W) and Chrysanthemum Crimson, Plate 824/3, page 169 (W); inside surface: between Cardinal Red, Plate 822, page 168 (W) and Chrysanthemum Crimson, Plate 824, page 169 (W). Outside surface: between Rose Madder, Plate 23, page 23 (W) and Rose Red, Plate 724/1, page 158 (W); inside surface: between Rose Red, Plate 724, page 158 (W) and Cardinal Red, Plate 822/2, page 168 (W).

*General color effect.*—Newly opened flower—between Currant Red, Plate 821/3, page 167 (W) and Cardinal Red, Plate 822/3, page 168 (W). 3-days open—between Cardinal Red, Plate 822/2, page 168 (W) and Chrysanthemum Crimson, Plate 824/1, page 169 (W).

*Behavior.*—Drop off cleanly; not particularly affected by cold, hot, wet or dry weather.

*Flower longevity.*—On bush in garden—4 to 5 days during August. Cut flowers grown outdoors and kept at living room temperature—from 5 to 7 days during August.

*Reproductive organs*

Stamens: From few to average number; arranged regularly about pistils; a few mixed with petaloids.

Filaments: From short to medium length (from 4 to 12 mm. long); most with anthers.

*Color.*—Near Crimson, Plate 22/3, page 22 (W).

Anthers: Medium size; all open approximately at once.

*Color.*—Near Cadmium Orange, Plate 8, page 8 (W). plate 7/2, page 7 (W), with remainder near Carmine, Plate 21/3, page 21 (W). Under side—margins near Saffron Yellow, Plate 7/2, page 7 (W), with remainder near Carmine, Plate 21/3, page 21 (W).

Pollen: Moderate abundance.

*Color.*—Near Cadmium Orange, Plate 8, page 8 (W).

Pistils: Average number (approximately 80).

Styles: Uneven; from short to average length; thin caliper; bunched.

*Color.*—Upper third of style near Carmine, Plate 21/1, page 21 (W), with remainder near Aureolin, Plate 3/3, page 3 (W).

Stigma:

*Color.*—Near Primrose Yellow, Plate 601/3, page 65 (W).

Ovaries: Usually all enclosed in calyx.

Hips: Average length; obovoid; smooth; walls thick and fleshy.

*Color (½ mature).*—Near Citron Green, Plate XXXI (R).

Sepals: Falling soon; medium length; straight.

*Color.*—Inside—near Light Grape Green, Plate XLI (R). Outside—near Absinthe Green, Plate XXXI (R).

Seeds: Average number (from 20 to 30); usually small size.

*Plant*

Foliage:

*Leaves.*—Compound of usually 3 to 7 leaflets; abundant; large; leathery; semi-glossy.

*Leaflets.*—Shape—oval. Apex—acute. Base—between round and obtuse. Margin—simply serrate.

*Color.*—Mature—upper surface: between Forest Green, Plate XVII (R) and Empire Green, Plate XXXII (R); under surface: near Chromium Green, Plate XXXII (R). Young—upper surface: near Deep Dull Yellow-Green (1), Plate XXXII (R), with edges of leaflets overlaid with near Dark Indian Red, Plate XXVII (R); under surface: near Light Yellowish Olive, Plate XXX (R) over laid with near Dark Indian Red, Plate XXVII (R).

*Rachis (the supporting stem of the compound leaf.*—From average to heavy in size. Under side —smooth grooved; with from none to few small stipitate glands on edges. Under side—smooth; with from none to few stipitate glands and few small prickles.

*Stipules.*—From short to medium length; medium width; with short points turning out at an angle of more than 45°.

*Disease resistance.*—Better than average resistance to mildew, as determined by comparison with other varieties grown under comparable cultural conditions at Ontario, California.

Growth:

*Habit.*—Upright-spreading; much branched.

*Growth.*—Very vigorous.

*Canes.*—Heavy.

*Main stems.*—Color—Yellowish Oil Green, Plate V (R). Large prickles—from several to many; medium length; almost straight; with narrow base of medium length; color: near Sayal Brown, Plate XXIX (R). Small prickles—few; color: near Sayal Brown, Plate XXIX (R). Hairs—none.

*Branches.*—Color—near Light Elm Green, Plate XVII (R). Large prickles—from several to many; from short to medium length; almost straight; with short, narrow base; color: near Pecan Brown, Plate XXVIII (R). Small prickles—from several to many; color: near Pecan Brown, Plate XXVIII (R). Hairs—none.

*New shoots.*—Color—near Absinthe Green, Plate XXXI (R) overlaid with near Ocher Red, Plate XXVII (R) on side exposed to sun. Large prickles—several; medium length; hooked slightly downward; with narrow base of medium length; color: near Lime Green, Plate XXXI (R). Small prickles—from few to several; color: near Lime Green, Plate XXXI (R). Hairs—none.

I claim:

A new and distinct variety of rose plant of the hybrid tea class, substantially as herein shown and described, characterized particularly as to novelty by the unique combination of a vigorous, upright-spreading and well branched plant habit, attractive, large, leathery and semi-glossy foliage, a habit of bearing the flowers usually singly and abundantly on relatively long and strong stems, the production of large, extremely double flowers having an attractive, gracefully irregular or wavy form reminiscent of old-fashioned roses, a distinctive and attractive Bright Red flower color, very long-lasting flower qualities, both as cut flowers and on the plant, with the ability of holding both the form and Bright Red color very well, and an ability of the flowers to clean well from the plant.

No references cited.

ABRAHAM G. STONE, *Primary Examiner.*